United States Patent [19]

de Haan et al.

[11] Patent Number: 5,709,881
[45] Date of Patent: Jan. 20, 1998

[54] TABLET CAPSULE OR GRANULE COMPRISING DESOGESTREL

[75] Inventors: Pieter de Haan; Johannes Gerardus Joseph Egberink, both of Oss, Netherlands

[73] Assignee: Akzo Nobel N.V., Arnhem, Netherlands

[21] Appl. No.: 864,435

[22] Filed: May 28, 1997

Related U.S. Application Data

[63] Continuation of Ser. No. 458,373, Jun. 2, 1995, abandoned.

[30] Foreign Application Priority Data

Jun. 8, 1994 [EP] European Pat. Off. ............... 94201625

[51] Int. Cl.$^6$ ................... A61K 9/14; A61K 9/20
[52] U.S. Cl. ............ 424/465; 424/401; 424/464; 424/472; 424/470; 424/489; 424/490
[58] Field of Search ................. 424/464, 401, 424/426, 465, 484, 451, 470, 488, 472, 489, 490

[56] References Cited

U.S. PATENT DOCUMENTS 4,948,593  8/1990  Wright et al. ............... 424/473
5,395,627  3/1995  Dopper et al. ............... 424/489

FOREIGN PATENT DOCUMENTS 0167825  1/1986  European Pat. Off. .
0368373  5/1990  European Pat. Off. .

*Primary Examiner*—Thurman K. Page
*Assistant Examiner*—Sharon Howard
*Attorney, Agent, or Firm*—William M. Blackstone

[57] ABSTRACT

The invention relates to a tablet, capsule, or granule for oral administration comprising desogestrel wherein desogestrel is mixed or dissolved in a solid selected from a lubricant free from organic solvents, and a waxy substance not being a lubricant.

6 Claims, No Drawings

TABLET CAPSULE OR GRANULE COMPRISING DESOGESTREL

This is a continuation of application Ser. No. 08/458,373 filed Jun. 2, 1995, now abandoned.

The invention relates to a tablet, capsule, or granule for oral administration comprising desogestrel.

Pharmaceutical compositions comprising desogestrel are known in the art, for example from U.S. Pat. No. 4,914,089. The known compositions comprising desogestrel, are however less suitable since desogestrel shows a tendency to migrate from granules comprising desogestrel. This is of particular concern since the granules comprise very low dosages of desogestrel. Tablets prepared from granules comprising desogestrel as active ingredient comprise usually 25–150 µg, and typically 25, 50, 75, 100, or 150 µg of desogestrel. A loss of for example 10% of the active substance within the shelf-life has therefore a dramatic effect on the amount of active ingredient in the tablet, and could lead to a tablet having less than the treshold amount of active ingredient to exert full activity. For desogestrel, which is used as active ingredient in contraceptive drugs, this is not acceptable in view of its safety and reliability. It is now found that a tablet, capsule, or granule for oral administration in which desogestrel is mixed or dissolved in a solid selected from a lubricant free from organic solvents, and a fatty substance not being a lubricant, is stable and has the ability to retain desogestrel even under extreme conditions.

Preferably desogestrel is mixed or dissolved in a solid selected from phospholipids, glycolipids, lipoproteins, hydrophilic or lipophylic waxy materials, fatty alcohols, polyethylene glycols, polyoxyethylene derivatives of sorbitan fatty acids, fatty acids or esters thereof, and mixtures thereof.

With more preference desogestrel is mixed or dissolved in a solid fatty acid or a monohydric alcohol ester or glycerol ester thereof.

Solid waxy excipients for dissolving or mixing desogestrel and the estrogen can be of a natural or synthetic source. Fats of vegetable origin consist mainly of (mixed) triglycerides. Examples of other suitable waxy excipients are stearic acid, stearyl alcohol, Precirol, magnesium stearate, hydrogenated castor oil (Cutina HR), hydrogenated arachis oil and lecithins. Emulsifying waxes are suitable for dispersing the active compounds. A typical example is the excipient Gelucire, which is composed of partial glycerides and polyglycides fatty esters, with controlled hydrophilic properties. Above-mentioned waxes may be mixed with additives. Specific examples of suitable additives for forming the solid are ethyl oleate, isopropyl myristate, cetyl palmitate, stearic acid, lecithins, sucrose polyester, Mygliol, Tween, glycerol, propylene glycols, and polyethylene glycols.

The pharmaceutical composition according to the invention may further comprise an estrogen. Examples of estrogens include ethinyl estradiol, mestranol (17-α-ethinyl estradiol 3-methylether), estrone, β-estradiol, estradiol valerate, and other compounds with estrogenic activity. Ethinyl estradiol is the preferred estrogen.

The solid matrix according to this invention prevents desogestrel from migration to the environment. It was further observed that desogestrel mixed or dissolved in a solid matrix comprising a waxy material, showed decreased decomposition.

The solid matrix can be processed into tablets, granules, and capsules and the like. Such processes are well-known in the art, and disclosed in standard references, such as Gennaro et al., Remington's Pharmaceutical Sciences, (18th ed., Mack Publishing Company, 1990, see especially Part 8: Pharmaceutical Preparations and Their Manufacture).

For incorporation of desogestrel and optionally an estrogen in the waxy phase in (a mixture of) waxy (or fatty) components other than lubricants, with an intermediate to high melting point (approx. >35° C.), it is most preferred to dissolve the active compound(s) together with the waxy (or fatty) components in a suitable organic solvent like acetone, ethanol or methanol. This solution can be distributed on a carrier material, consisting of a composite granulate or of a single component like crystalline lactose. After evaporation of the solvent, the drug loaded carrier can, if necessary, be admixed with adjuvants to optimize flowability of the carrier (colloidal silicon dioxide) and/or with lubricating agents (for instance magnesium stearate). The resulting drug-loaded mixture can be granulated or compressed to tablets or be filled into gelatin or starch capsules. For the preparation of a homogeneous mixture of the low-dose drugs with waxy compounds with a relatively high melting point (>45° C.), such as lubricants, a mixture can also be prepared without the use of solvents, after which the same above-described further procedure can be followed. The micronized drugs have to be intimately mixed using procedures and equipment allowing high shear forces. The obtained mixture can be diluted with conventional excipients and processed to capsules, granules or tablets applying conventional techniques. Moreover, it is possible to directly cool down the liquidified molten dispersion of the active ingredients in the waxy substance and subsequently to screen the solid material to a small particle size for further processing in a mixture for tableting or capsulating.

The solid matrix comprising desogestrel comprises the usual excipients like carriers, diluents, lubricants, and binders. The solid matrix can be processed as granules. General methods of preparing granules are for instance described in Pharmaceutical Dosage Forms: Tablets (Volume 1). Ed. H. A. Lieberman, L. Lachman and J. B. Schwartz (1989), Marcel Dekker Inc., New York and Basel, pp. 131–190.

Preferably the solid matrix comprising desogestrel will also include a disintegrating agent.

Diluents or filler excipients are agents added to dosage units to increase the granules and resulting dosage units bulk. The preferred diluent for use in this regard is lactose. Other diluents include mannitol, sorbitol, cellulose, xylitol, dextrose, fructose, calcium phosphate, $NaCaPO_4$, sucrose, and mixtures thereof. The diluent will typically make up from 70 to 95% by weight of the resulting steroid loaded granules.

Binders are agents used to impart cohesive properties to the granules, resulting in more physically stable dosage units, and include hydroxypropylcellulose (HPC), amylopectin, starch, hydroxypropylmethylcellulose (HPMC), gelatin, and starch based binders. The preferred binder for use with the invention is HPC or povidone (polyvinylpyrrolidone). The binder will typically make up from 0.5 to 5% by weight of the resulting steroid loaded granules.

Disintegrating agent or disintegrators are substances or mixtures of substances added to a tablet to facilitate its breakup or disintegration after administration.

Typically such agents are modified or unmodified starches, clays, cross-linked PVP, modified or unmodified celluloses, gums or algins. The presently most preferred agents are corn starch, potato starch, and wheat starch. Disintegrators will typically make up from 5 to 50%, preferably 5 to 15%, by weight of the resulting granules.

Lubricants, in the conventional manner used, are agents which improve the rate of flow of the tablet granulation, prevent adhesion of the tablet material to the surface of dies and punches, reduce interparticle friction, and facilitate the ejection of the tablets from the die cavity. Commonly used lubricants are talc, long chain fatty acids, magnesium stearate, stearic acid, calcium stearate, polyethylene glycol, palmitic acid, and hydrogenated vegetable oils. The lubricant will typically make up from 0.25 to 3% by weight of the resulting granules. According to this invention solid lubricants can also be used as an excipient for mixing or dissolving with the active ingredient without using organic solvents.

The use of other conventional additives or further excipients, e.g. colorants, stabilizers or anti-oxidants, is contemplated. Stabilizers such as EDTA, polyethylene glycol (PEG), and butylated hydroxytoluene (BHT), may also be included if desired, although it is not required. The presently most preferred anti-oxidant for use with the invention is dl-α-tocopherol. Other medicinal agents (for instance 17β-estradiol) may also be included in the formulation.

The invention is further illustrated by the following examples.

EXAMPLE 1

Sublimation properties of desogestrel in a solid matrix according to the invention were compared with sublimation properties of desogestrel with excipients of the art. Desogestrel (1.5 mg) was mixed with 600 mg of excipient. Samples were stored for 72 h at 70° C. under a pressure of 15 kPa (150 mbar). Sublimation vapours were collected on a cold finger at 4° C., and the amount of desogestrel sublimed was analyzed quantitatively.

| desogestrel mixture with | amount of desogestrel sublimed (% of quantity in starting mixture) |
|---|---|
| prior art: | |
| lactose | 25 |
| micro-crystalline cellulose | 22 |
| this invention: | |
| cutina-HR wax | 2 |
| stearic acid | 0.5 |

EXAMPLE 2

Lactose (130.5 kg) and starch (15 kg) were loaded into the bowl of a fluid bed granulator and blended. The blend was granulated by spraying a binder solution containing polyvidone (4.5 kg) in water (13.5 l) onto the bed. After completion of spraying, the granulate was dried and screened. 1.952 Kg of this granulate were loaded in the bowl of a high shear mixer and heated to 50°–60° C. In a separate vessel stearic acid (20 g) was molten and heated to 110° C. Desogestrel (4.75 g), ethinyl estradiol ((0.923 g) and dl-α-tocopherol (2.462 g) were added and dissolved. The clear warm solution was added to the granulate in the high shear mixer and mixed for 3–5 min. After mixing the granulate was cooled to room temperature and colloidal silicon dioxide (20 g) was admixed with the granulate. The granulate was compressed into cores with a mass of 65 mg and a diameter of 5 mm. Tablet cores (1 kg) were film coated in a side-vented coating pan using 230 g of a coating suspension containing 50 g of hydroxypropyl methylcellulose, 10 g of polyethylene glycol 400, 7.5 g of titanium dioxide, and 12.5 g of talc in 920 ml of purified water.

We claim:

1. A pharmaceutical composition free from organic solvents in a solid matrix for oral administration comprising desogestrel mixed or dissolved in a solid selected from a lubricant, a waxy substance that is not a lubricant and mixtures thereof.

2. The pharmaceutical composition of claim 1, wherein desogestrel is mixed or dissolved in a solid selected from the group consisting of phospholipids, glycolipids, lipoproteins, hydrophilic waxy materials, lipophylic waxy materials, fatty alcohols, polyethylene glycols, polyoxyethylene derivatives of sorbitan fatty acids, esters of fatty acids, and mixtures of two or more thereof.

3. The pharmaceutical composition of claim 1, wherein desogestrel is mixed with or dissolved in a solid fatty acid or a monohydric alcohol ester or glycerol ester thereof.

4. The pharmaceutical composition of claim 1 further comprising an estrogen.

5. A method for reducing desogestrel migration from a pharmaceutical composition for oral administration comprising desogestrel, comprising mixing or dissolving desogestrel in a solid selected from a lubricant and a waxy substance that is not a lubricant that are free from organic solvents.

6. A method of incorporation of desogestrel into a solid pharmaceutical composition, comprising combining desogestrel with a solid lubricant in the absence of organic solvents or a waxy substance not being a lubricant in the absence of organic solvents, and applying the combination to a carrier material to make a solid matrix.

* * * * *